United States Patent [19]

Tjoeng et al.

[11] Patent Number: 5,707,984

[45] Date of Patent: Jan. 13, 1998

[54] STEROID NITRITE/NITRATE ESTER DERIVATIVES USEFUL AS ANTI-INFLAMMATORY DRUGS

[75] Inventors: Foe S. Tjoeng, Manchester; Mark G. Currie, St. Charles, both of Mo.; Mark E. Zupec, O'Fallon, Ill.

[73] Assignee: G. D. Searle & Co., Chicago, Ill.

[21] Appl. No.: 569,812

[22] Filed: Dec. 8, 1995

[51] Int. Cl.$^6$ .............. A61K 31/57; C07J 7/00; C07J 17/00; C07J 43/00

[52] U.S. Cl. .............. 514/179; 552/564; 552/581; 514/180; 540/108; 540/111; 540/114; 540/115

[58] Field of Search .............. 552/582, 585, 552/586, 587, 588, 589, 590, 591, 592, 593, 594, 595, 596, 597, 598, 599, 600, 601, 602, 603, 604, 605, 607, 608, 609, 610, 611; 540/108, 111, 114, 115

[56] References Cited

U.S. PATENT DOCUMENTS

| | | | |
|---|---|---|---|
| 3,215,713 | 11/1965 | Barton | 260/397.4 |
| 3,298,941 | 1/1967 | Barton | 204/158 |
| 3,639,434 | 2/1972 | Oxley et al. | 260/397.45 |
| 3,743,741 | 7/1973 | Laurent et al. | 424/242 |
| 3,839,369 | 10/1974 | Hofmeister et al. | 260/397.45 |
| 3,930,970 | 1/1976 | Barton | 204/158 |

FOREIGN PATENT DOCUMENTS

| | | | |
|---|---|---|---|
| 969927 | 6/1975 | Canada. | |
| 975755 | 10/1975 | Canada. | |
| 2222491 | 5/1972 | Germany | C07C 169/34 |
| 1643034 | 8/1976 | Germany. | |
| DE4223800 A1 | 1/1994 | Germany. | |
| 1082573 | 9/1967 | United Kingdom. | |
| 1082574 | 9/1967 | United Kingdom. | |
| WO9403421-A2 | 2/1997 | WIPO. | |

OTHER PUBLICATIONS

Bucknell et al., *Journal of the Chemical Society, Perkin Transactions 2*, No. 3, 401–403 (1994).
Cederqvist et al., *Biochemical Pharmacology*, vol. 46, No. 6, 1047–1053 (1994).
Kowaluk et al., *Journal of Pharmacology and Experimental Therapeutics*, vol. 259, No. 2, 519–525 (1991).
Moncada et al., *Biochem. Pharm.* 38 : 1709–1715 (1989).
Moncada et al., *Pharm. Review* 43 : 109–147 (1991).
Moncada et al., *Jour. Cardio. Pharm* 17 : 525 (1991).
Persson et al., *Eur. Jour. Pharm.* 249 R7–R8 (1993).
Alspaugh & Granger, *Infection and Immunity*, 59 : 2291–2296 (1991).
Wallace et al., *Eur. Jour. Pharm.* 257 : 249–255 (1994).
MacIntyre et al., *Proc. Nat. Acad. Sci.* USA 88 2936–2940 (1991).
Pipili–Synetos et al., *British Jornal of Pharmacology*, 116, 1829–1834 (1995).

*Primary Examiner*—José G. Dees
*Assistant Examiner*—Barbara Badio
*Attorney, Agent, or Firm*—Dennis A. Bennett

[57] ABSTRACT

Disclosed are steroid nitrite/nitrate ester derivatives of formula I:

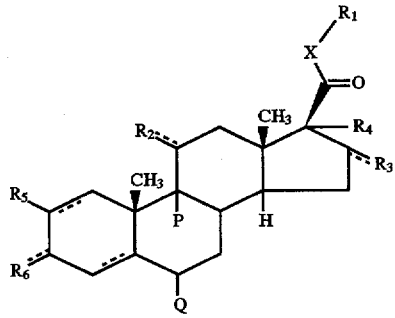

wherein, the substituents are as defined in the specification and their use in the treatment of inflammatory diseases.

12 Claims, 2 Drawing Sheets

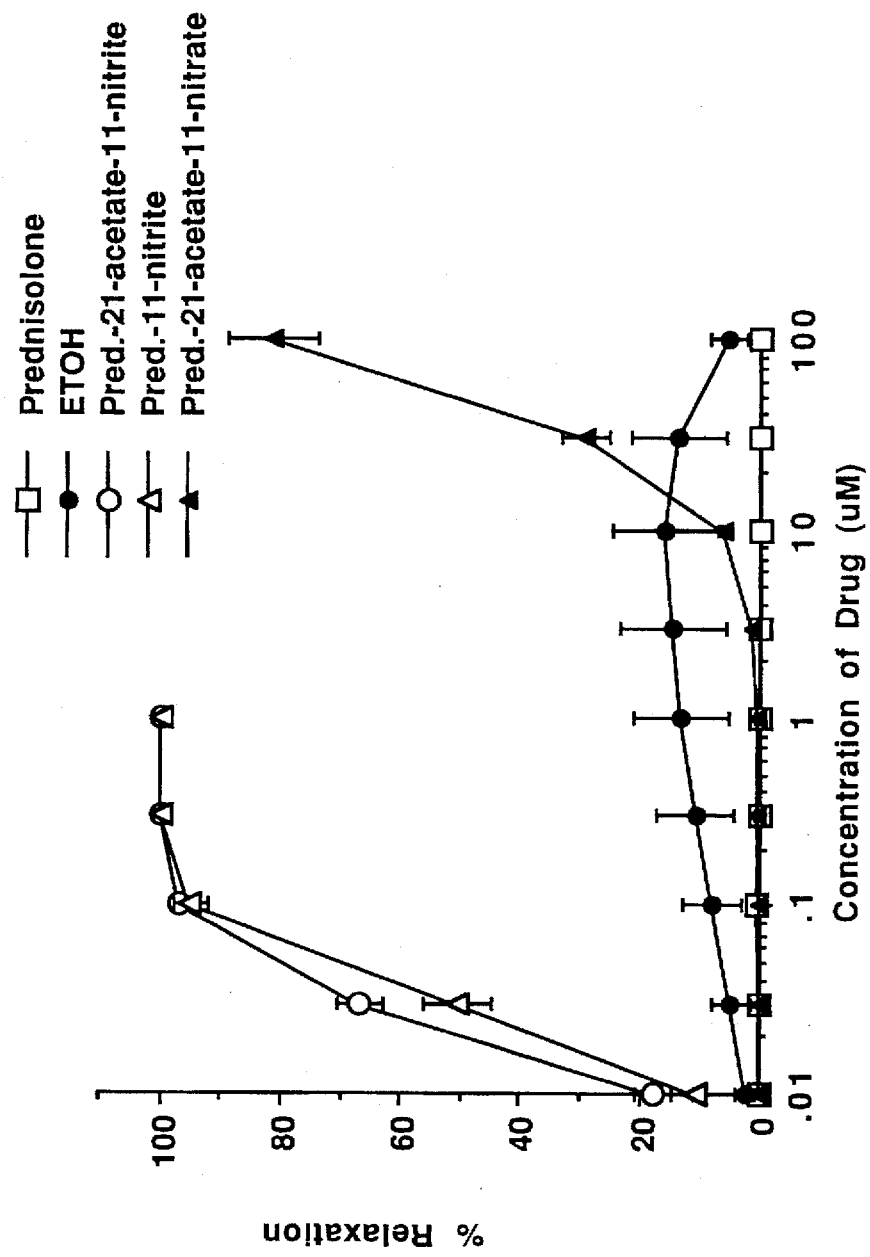

STEROID NITRITE/NITRATE ESTER DERIVATIVES USEFUL AS ANTI-INFLAMMATORY DRUGS

BACKGROUND OF THE INVENTION

1. Field of the Invention

The present invention relates to novel steroid nitrite/nitrate ester derivatives, and to their use treating inflammatory diseases.

2. Related Art

Steroids, specifically of the glucocorticoid class of molecules, are known to possess anti-inflammatory and immunomodulatory activities and are commonly utilized for the treatment of numerous autoimmune and inflammatory diseases. However, their beneficial effects are often slow to develop and accompanied by many dose-limiting side-effects. Nitric oxide donors, such as nitroglycerin, have also been utilized as pharmaceutical agents with prominent beneficial effects on the cardiovascular system. Many of the biological actions of nitric oxide potentially counteract the side-effects of the glucocorticoids and may enhance their therapeutic actions. The present invention relates to novel steroid nitrite/nitrate ester derivatives that possess the combined biological properties of glucocorticoids and nitric oxide donors in a single molecule. These molecules have an advantage over currently utilized glucocorticoids in that they rapidly elicit beneficial pharmacological effects, such as bronchial relaxation, through the release of nitric oxide. It is intended that these novel molecules be utilized for therapy, in particular their use as anti-inflammatory and immunosuppressive drugs for the treatment of rheumatic diseases, immunological disorders, skin disorders, inflammation, transplant rejection, cancer, osteoporosis, rhiniris and asthma with lowered side-effects.

Glucocorticoids are commonly utilized for the pharmacologic treatment of inflammation and undesirable immune system reactions. These steroids have the capacity to prevent or suppress the development of inflammation resulting from a number of different injurious agents including infectious, immunological, chemical, mechanical, and radiation. Glucocorticoids are also effective in the treatment of immune system disorders including autoimmune diseases such as rheumatoid arthritis and lupus, and transplant rejection. However, the therapeutic applications of these steroids are somewhat limited due to toxicity and side-effects. The major side effects of the glucocorticoids are hypertension, peptic ulcers, increased susceptibility to infections, osteoporosis, hyperglycemia, and vascular occlusion.

It has been known since the early 1980's that the vascular relaxation brought about by acetylcholine is dependent on the presence of the endothelium and this activity was ascribed to a labile humoral factor termed endothelium-derived relaxing factor (EDRF). The activity of nitric oxide (NO) as a vasodilator has been known for well over 100 years and NO is the active component of amylnitrite, glyceryltrinitrate and other nitrovasodilators. The recent identification of EDRF as NO has coincided with the discovery of a biochemical pathway by which NO is synthesized from the amino acid L-arginine by the enzyme nitric oxide synthase. The NO released by the constitutive enzyme acts as a transduction mechanism underlying several physiological responses. The NO produced by the inducible enzyme is a cytotoxic molecule for tumor cells and invading microorganisms.

NO is the endogenous stimulator of the soluble guanylate cyclase and is involved in a number of biological actions in addition to endothelium-dependent relaxation including cytotoxicity of phagocytic cells and cell-to-cell communication in the central nervous system (see Moncada et al, Biochemical Pharmacology, 38, 1709– 1715 (1989) and Moncada et al, Pharmacological Reviews, 43, 109–142 (1991). Furthermore, NO has been shown to posses antithrombotic (see Moncada et al. Journal of Cardiovascular Pharmacology 17, S25 (1991), Byrne et al., World Patent application WO9403421-A2 and Schonafinger et al., German Patent application DE4223800-A1), bronchorelaxant (Persson et al. European Journal of Pharmacology, 249, R7–R8 (1993), antiinflammatory, microbialcidal (Alspaugh and Granger, Infection and Immunity 59, 2291–2296 (1991) and gastroprotective (see Wallace et al. European Journal of Pharmacology, 257, 249–255 (1994) effects in animal models. In addition, nitric oxide has been suggested to be effective against the loss of bone in in vitro models of osteoporosis (MacIntyre et al. Proc. Natl. Acad. Sci. USA 88, 2936–2940 (1991) and in inhibiting angiogenesis, tumour growth and metastasis in in vivo animal models (Pipili-Synetos et al. British Journal of Pharmacology, 116, 1829–1834 (1995). In U.S. Pat. Nos. 3,930,970, 3,298,941 and 3,215,713, a novel photochemical process for the preparation of diol mononitrates from alcohol nitrites is disclosed. In U.S. Pat. Nos. 3,639,434, 3,743,741 and 3,839,369, the preparation of steroid nitrate esters and their uses as intermediates is disclosed. In German Patent 1643034, a method for the preparation of steroid nitrate esters is disclosed. In Canadian Patents 975755 and 969927, a process for the preparation and acidolysis of nitrate esters of 21-alcohols of the pregnane series is disclosed, respectively. In British Patent 1,082,573 and 1,082,574, a process for the preparation of steroid-11-nitrate esters and their uses as intermediates is disclosed.

Thus, these properties make nitric oxide an ideal agent to enhance the actions of corticosteroids in the treatment of various diseases mentioned earlier by both increasing their biological effects as well as by reducing their side effects. The present invention relates to novel nitrite esters of steroids, processes for their preparation, pharmaceutical compositions containing them, and methods for their use.

SUMMARY OF THE INVENTION

The present invention concerns steroid nitrite derivatives of the Formula I.

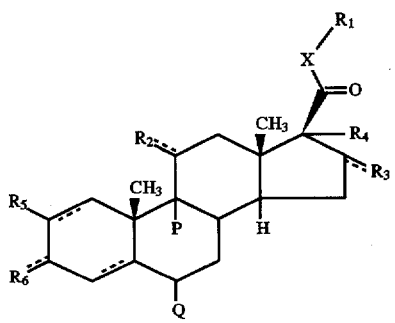

and pharmaceutically acceptable ester and prodrugs thereof, wherein the dotted lines indicate a single or a double bond;

$R_1$ is selected from the group consisting of hydrogen, hydroxy, nitrite ester (ONO), nitrate ester ($ONO_2$), halogen, haloalkyl, nitroxyalkanoyl, sulfhydryl, lower thioalkyl, heterocyclic, lower alkoxy, alkylsilyloxy, lower alkyl, lower alkenyl and lower alkynyl wherein all said radicals may optionally be substituted with hydroxy, halogen, lower alkyl, lower alkenyl, lower alkynyl, lower alkoxy, amino, nitro, nitril, carboxyl and haloalkyl radicals; and OCO—$R_7$ wherein $R_7$ is alkanoic acid, lower alkyl, lower alkenyl, lower alkynyl, or lower alkoxy;

$R_2$ is selected from the group consisting of hydrogen, hydroxy, oxygen, nitrite ester (ONO), nitrate ester (ONO$_2$), nitroxyalkanoyl, lower alkoxy, alkylsilyloxy, and lower alkyl wherein all said radicals may optionally be substituted with hydroxy, lower alkyl, lower alkenyl, lower alkynyl, lower alkoxy, amino, nitro, nitril, carboxyl haloalkyl radicals and OCO—$R_8$ wherein $R_8$ is alkanoic acid, lower alkyl, lower alkenyl, lower alkinyl or lower alkoxy group;

$R_3$ and $R_4$ are independently selected from the group consisting of hydrogen, hydroxy, nitrite ester (ONO), nitrate ester (ONO$_2$), nitroxyalkanoyl, lower alkyl, lower alkenyl, lower alkynyl, lower alkoxy, wherein all said radicals may optionally be substituted with hydroxy, lower alkyl, lower alkenyl, lower alkynyl, lower alkoxy, amino, nitro, nitril, carboxyl and haloalkyl radicals, and OCO—$R_9$ wherein $R_9$ is 2-furanyl, lower alkyl or lower alkoxy group;

$R_5$ is hydrogen or halogen;

$R_6$ is hydrogen, hydroxy, or oxygen;

P and Q are independently selected from the group consisting of hydrogen, halogen or lower alkyl;

X is a lower alkyl group or sulfur if $R_1$ is a haloalkyl; and with the proviso that at least one of the following $R_1$, $R_2$, $R_3$ or $R_4$ is a nitrite ester (ONO) and that at least one of the following $R_1$, $R_2$, $R_3$ or $R_4$ is nitrate ester (ONO2).

The invention further relates to pharmaceutical compositions comprising a compound of formula I. Compounds and pharmaceutical compositions defined above have usefulness as antiinflammatory and immunosuppressive drugs for treatment of rheumatic diseases, immunological disorders, skin disorders, inflammation, transplant rejection, osteoporosis, cancer, rhinitis and asthma. These compounds combine the previously described actions of the steroids and NO in a single molecule. The novel compounds of the present invention may exert their steroid activities directly with the NO still attached or after the NO is released, whereby the compound is converted back to its parent steroid.

BRIEF DESCRIPTION OF THE DRAWING

FIG. 2 shows the effect on Aortic Ring Relaxation of the title compound in Example 1 and 2.

DETAILED DESCRIPTION OF THE INVENTION

Figure 1:
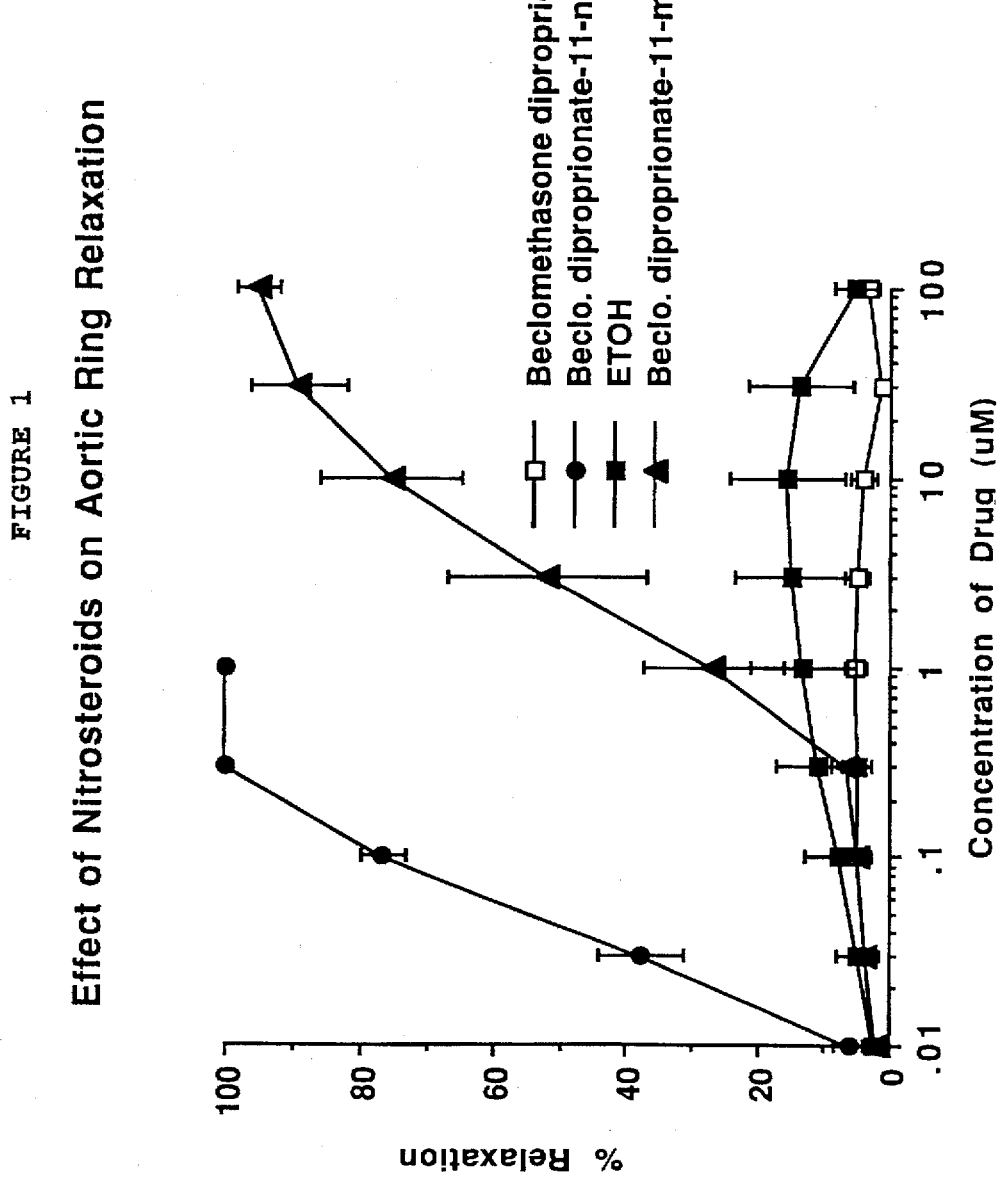
FIG. 1 shows the effect on Aortic Ring Relaxation of the title compound in Example 11.

A preferred embodiment of the present invention is a compound of the formula (I):

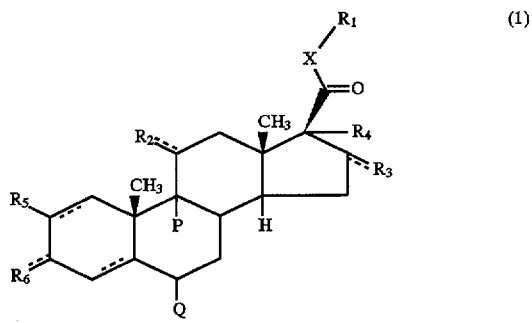

wherein the dotted lines indicate a single or a double bond;

$R_1$ is selected from the group consisting of hydrogen, hydroxy, nitrite ester (ONO), nitrate ester (ONO$_2$), halogen, haloalkyl, heterocyclic group of 2 to 5 carbon atoms and 1 to 2 hetero atoms, nitroxyalkanoyl group of 2 to about 6 carbon atoms, sulfhydryl, lower thioalkyl group of 1 to about 6 carbon atoms, lower alkoxy group of 1 to about 6 carbon atoms, alkylsilyloxy group of 3 to about 8 carbon atoms, lower alkyl group of 1 to about 6 carbon atoms, wherein all said radicals may optionally be substituted with hydroxy, halogen, lower alkyl, lower alkenyl, lower alkynyl, lower alkoxy, amino, nitro, nitril, carboxyl and haloalkyl radicals, OCO—$R_7$ wherein $R_7$ is alkanoic acid group of 2 to about 6 carbon atoms, lower alkyl group of 1 to about 6 carbon atoms, lower alkenyl group of 2 to about 6 carbon atoms, lower alkynyl group of 2 to about 6 carbon atoms, or lower alkoxy group of 1 to about 6 carbon atoms group;

$R_2$ is selected from the group consisting of hydrogen, hydroxy, oxygen, nitrite ester (ONO), nitrate ester (ONO$_2$), nitroxyalkanoyl group of 2 to about 6 carbon atoms, lower alkoxy group of 1 to about 6 carbon atoms, alkylsilyloxy group of 3 to about 8 carbon atoms, lower alkyl group of 1 to about 6 carbon atoms, wherein all said radicals may optionally be substituted with hydroxy, lower alkyl, lower alkenyl, lower alkynyl, lower alkoxy, amino, nitro, nitril, carboxyl and haloalkyl radicals, OCO—$R_8$ wherein $R_8$ is alkanoic acid group of 2 to about 6 carbon atoms, lower alkyl group of 1 to about 6 carbon atoms, lower alkenyl group of 2 to about 6 carbon atoms, lower alkynyl group of 2 to about 6 carbon atoms or lower alkoxy group of 1 to about 6 carbon atoms group;

$R_3$ and $R_4$ are independently selected from the group consisting of hydrogen, hydroxy, nitrite ester (ONO), nitrate ester (ONO$_2$), nitroxyalkanoyl group of 2 to about 6 carbon atoms, lower alkyl group of 1 to about 6 carbon atoms, lower alkenyl group of 2 to about 6 carbon atoms, lower alkynyl group of 2 to about 6 carbon atoms, lower alkoxy group of 1 to about 6 carbon atoms, wherein all said radicals may optionally be substituted with hydroxy, lower alkyl, lower alkenyl, lower alkynyl, lower alkoxy, amino, nitro, nitril, carboxyl and haloalkyl radicals; and a group of formula OCO—$R_9$ wherein $R_9$ is 2-furanyl, lower alkyl group of 1 to about 6 carbon atoms or lower alkoxy group of 1 to about 6 carbon atoms;

$R_5$ is hydrogen, or halogen;

$R_6$ is hydrogen, hydroxy, or oxygen;

P and Q are independently selected from a group consisting of hydrogen, chloro, fluoro and alkyl group of 1 to about 6 carbon atoms;

X is lower alkyl group, or sulfur if $R_1$ is a haloalkyl; and with the proviso that at least one of the following $R_1$, $R_2$, $R_3$ or $R_4$ is a nitrite ester (ONO) and that at least one of the following $R_1$, $R_2$, $R_3$ or $R_4$ is nitrate ester (ONO2).

Another preferred embodiment of the present invention is a compound of the formula (I):

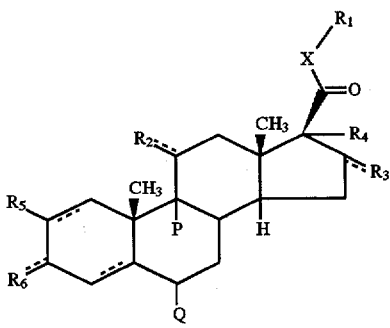

(1)

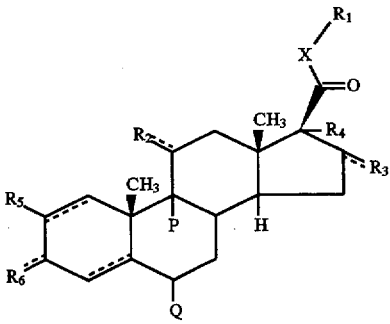

(1)

wherein;

the dotted lines indicate a single or a double bond;

$R_1$ is selected from the group consisting of hydrogen, hydroxy, nitrite ester (ONO), nitrate ester ($ONO_2$), halogen, haloalkyl, sulfhydryl, heterocyclic group of 3 to 4 carbon atoms and 1 to 2 hetero atoms, nitroxyalkanoyl group of 2 to about 4 carbon atoms, lower alkoxy group of 1 to about 4 carbon atoms, alkylsilyloxy group of 3 to about 6 carbon atoms, lower alkyl group of 1 to about 4 carbon atoms, wherein all said radicals may optionally be substituted with hydroxy, chloro, fluoro, lower alkyl, lower alkenyl, lower alkynyl, lower alkoxy, amino, nitro, nitril, carboxyl, haloalkyl radicals and OCO—$R_7$ wherein $R_7$ is alkanoic acid group of 2 to about 4 carbon atoms, lower alkyl group of 1 to about 4 carbon atoms, lower alkenyl group of 2 to about 4 carbon atoms, lower alkynyl group of 2 to about 4 carbon atoms, or lower alkoxy group of 1 to about 4 carbon atoms group;

$R_2$ is selected from the group consisting of hydrogen, hydroxy, oxygen (ketone), nitrite ester (ONO), nitrate ester ($ONO_2$), nitroxyalkanoyl group of 2 to about 4 carbon atoms, lower alkoxy group of 1 to about 4 carbon atoms, and lower alkyl group of 1 to about 4 carbon atoms, wherein all said radicals may optionally be substituted with hydroxy, lower alkyl, lower alkenyl, lower alkynyl, lower alkoxy, amino, nitro, nitril, carboxyl, haloalkyl radicals; and OCO—$R_8$ wherein $R_8$ is alkanoic acid group of 2 to about 4 carbon atoms, lower alkyl group of 1 to about 4 carbon atoms, lower alkenyl group of 2 to about 4 carbon atoms, lower alkynyl group of 2 to about 4 carbon atoms or lower alkoxy group of 1 to about 4 carbon atoms;

$R_3$ and $R_4$ are independently selected from the group consisting of hydrogen, hydroxy, nitrite ester (ONO), nitrate ester ($ONO_2$), nitroxyalkanoyl group of 2 to about 4 carbon atoms, lower alkyl group of 1 to about 4 carbon atoms, lower alkenyl group of 2 to about 4 carbon atoms, lower alkynyl group of 2 to about 4 carbon atoms, and lower alkoxy group of 1 to about 4 carbon atoms, wherein all said radicals may optionally be substituted with hydroxy, lower alkyl, lower alkenyl, lower alkynyl, lower alkoxy, amino, nitro, haloalkyl radicalsand OCO—$R_9$ wherein $R_9$ is 2-furanyl, lower alkyl group of 1 to about 4 carbon atoms or lower alkoxy group of 1 to about 4 carbon atoms;

$R_5$ is hydrogen or halogen;

$R_6$ is hydrogen, hydroxy, or oxygen;

P and Q are independently selected from a group consisting of hydrogen, chloro, fluoro and alkyl group of 1 to about 4 carbon atoms;

X is a methylene group, or sulfur if $R_1$ is a fluoromethyl group;

with the proviso that at least one of the following $R_1$, $R_2$, $R_3$ or $R_4$ is a nitrite ester (ONO) and that at least one of the following $R_1$, $R_2$, $R_3$ or $R_4$ is nitrate ester ($ONO_2$).

Another preferred embodiment of the present invention is a compound of the formula (I):

the dotted lines indicate a single or a double bond;

$R_1$ is selected from the group consisting of hydrogen, hydroxy, nitrite ester (ONO), nitrate ester ($ONO_2$), chloro, sulfhydryl, N-methylpiperazin-1-yl, trimethylsilylmethyloxy, t-butyldimethylsilyloxy, lower alkyl group of 1 to about 4 carbon atoms and OCO—$R_7$ wherein $R_7$ is propanoic acid, methyl or ethyl group;

$R_2$ is selected from the group consisting of hydroxy, oxygen, nitrite ester (ONO), or nitrate ester ($ONO_2$);

$R_3$ and $R_4$ are independently selected from the group consisting of hydrogen, hydroxy, nitrite ester (ONO), nitrate ester ($ONO_2$), methyl, and OCO—$R_9$ wherein $R_9$ is ethoxy, methyl, or ethyl;

$R_5$ is hydrogen;

$R_6$ is hydroxy or oxygen;

P and Q are independently selected from a group consisting of hydrogen, chloro, fluoro and methyl group;

X is methylene; and with the proviso that at least one of the following $R_1$, $R_2$, $R_3$ or $R_4$ is a nitrite ester (ONO) and that at least one of the following $R_1$, $R_2$, $R_3$ or $R_4$ is nitrate ester (ONO2).

While it may be possible for the preparations or compounds as defined above to be administered as the raw chemical, it is preferable to present them as a pharmaceutical formulation. According to a further aspect, the present invention provides a pharmaceutical formulation comprising a preparation or a compound as defined above or a pharmaceutically acceptable salt or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a preparation or a compound as defined above or a pharmaceutically acceptable salt or solyarc thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

Formulations for administration by inhalation can be prepared for use as an aerosolized medicaments such as in the manner recited in U.S. Pat. No. 5,458,135 and U.S. Pat. No. 5,447,150.

Preferred unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

The compounds of the invention may be administered orally or via injection at a dose of from 0.01 to 500 mg/kg per day. The dose range for adult humans is generally from 0.1 mg to 1 g/day. Tablets or other forms of presentation provided in discrete units may conveniently contain an amount of compound of the invention which is effective at such dosage or as a multiple of the same, for instance, units containing 0.05 mg to 250 mg, usually around 0.1 mg to 100 mg.

The compounds of formula (I) are preferably administered orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

As utilized herein, the term "lower alkyl", alone or in combination, means an acyclic alkyl radical containing from 1 to about 10, preferably from 1 to about 8 carbon atoms and more preferably 1 to about 6 carbon atoms. Examples of such radicals include methyl, ethyl, n-propyl, isopropyl, n-butyl, isobutyl, sec-butyl, tert-butyl, pentyl, iso-amyl, hexyl, octyl and the like.

The term "lower alkenyl" refers to an unsaturated acyclic hydrocarbon radical in so much as it contains at least one double bond. Such radicals containing from about 2 to about 10 carbon atoms, preferably from about 2 to about 8 carbon atoms and more preferably 2 to about 6 carbon atoms. Examples of suitable alkenyl radicals include propylenyl, buten-1-yl, isobutenyl, penten-1-yl, 2-2-methylbuten-1-yl, 3-methylbuten-1-yl, hexen-1-yl, hepten-1-yl, and octen-1-yl, and the like.

The term "lower alkynyl" refers to an unsaturated acyclic hydrocarbon radicals in so much as it contains one or more triple bonds, such radicals containing about 2 to about 10 carbon atoms, preferably having from about 2 to about 8 carbon atoms and more preferably having 2 to about 6 carbon atoms. Examples of suitable alkynyl radicals include ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethylbutyn-1-yl radicals and the like.

The term "alicyclic hydrocarbon" means an aliphatic radical in a ring with 3 to about 10 carbon atoms, and preferably from 3 to about 6 carbon atoms. Examples of suitable alicyclic radicals include cyclopropyl, cyclopropylenyl, cyclobutyl, cyclopentyl, cyclohexyl, 2-cyclohexen-1-ylenyl, cyclohexenyl and the like.

The term "heterocyclic" means a saturated or unsaturated cyclic hydrocarbon radical with 2 to about 10 carbon atoms, preferably about 4 to about 6; wherein 1 to about 3 carbon atoms are replaced by nitrogen, oxygen or sulfur. The "heterocyclic radical" may be fused to an aromatic hydrocarbon radical. Suitable examples include pyrrolyl, pyridinyl, pyrazolyl, triazolyl, pyrimidinyl, pyridazinyl, oxazolyl, thiazolyl, imidazolyl, indolyl, thiophenyl, furanyl, tetrazolyl, 2-pyrrolinyl, 3-pyrrolinyl, pyrrolindinyl, 1,3-dioxolanyl, 2-imidazonlinyl, imidazolidinyl, 2-pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3, 5-trithianyl, benzo(b)thiophenyl, benzimidazolyl, quinolinyl, and the like.

The term "lower alkoxy", alone or in combination, means an alkyl ether radical wherein the term alkyl is as defined above and most preferably containing 1 to about 4 carbon atoms. Examples of suitable alkyl ether radicals include methoxy, ethoxy, n-propoxy, isopropoxy, n-butoxy, iso-butoxy, sec-butoxy, tert-butoxy and the like.

The term "lower thioalkyl" means the same as "alkoxy" except sulfur replaces oxygen.

The term "alkylsilyloxy" means alkylsilyl ether radical wherein the term alkyl is as defined above and most preferably containing 3 to 8 carbon atoms. Examples of suitable alkylsilyl ether radicals include trimethylsilyl, t-butyldimethylsilyl, and the like.

The term "halogen" means fluorine, chlorine, bromine or iodine.

The term "haloalkyl" means a lower alkyl as defined above having 1–5 preferably 1–3 halogens attached to said lower alkyl chain.

The term "prodrug" refers to a compound that is made more active in vivo.

As used herein, reference to "treatment" of a patient is intended to include prophylaxis.

All references, patents or applications, U.S. or foreign, cited in the application are hereby incorporated by reference as if written herein.

Starting materials used to make the present invention are commercially available such as from Sigma, Fluka and Aldrich Chemical Company.

A general synthetic scheme is outlined below for the compounds of the present invention.

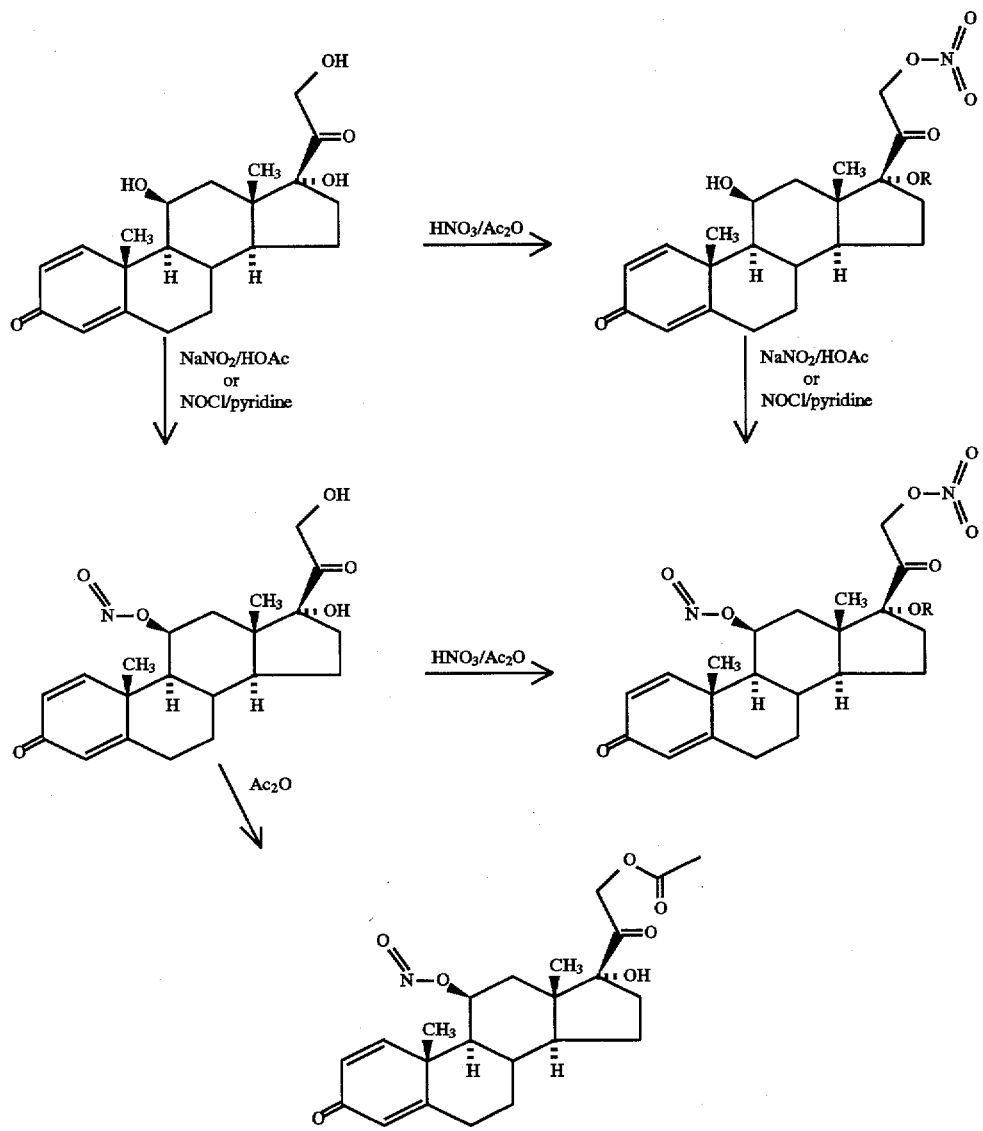

SCHEME I

50

It will be obvious to one skilled in the art to make modifications in the choice of starting materials and process conditions to make all of the invention compounds disclosed herein.

The invention is illustrated by the following examples:

EXAMPLE 1

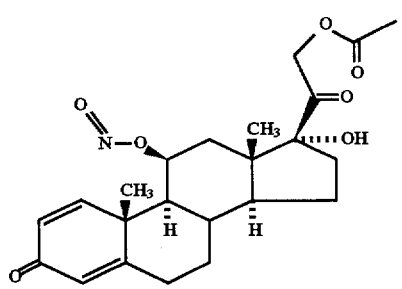

Prednisolone-21-acetate (0.4 g; 1 mmole), amylnitrite ester (0.36 g; 3 mmoles) and acetic acid (2 drops) were stirred in dioxane (10 ml) and dimethylsulfoxide (1 ml) at room temperature over weekend. The mixture was poured into water (50 ml) and extracted with dichloromethane (3×10 ml). The combined organic phase was dried over sodium sulfate and filtered. The filtrate was taken down to dryness under reduced pressure and the residue purified on a Waters Deltapak column (15 cm×2.5 cm) using a linear gradient of 5–70% acetonitrile/water/trifluoroacetic acid. FAB-MS: (M+Li)$^+$=438; $^1$H-NMR (DMSO-d$_6$) d 0.76 (s, 3H, CH$_3$ (C-18)), 1.37 (s, 3H, CH$_3$ (C-19)), 2.05 (s, 3H, CH$_3$CO), 4.7–4.9 (q, 2H, CO—CH$_2$—O), 5.6 (s, 1H, CH(C-11)), 5.98 (s, 1H, CH(C-4)), 6.2 (d, 1H, CH(C-2)), 7.0 (d, 1H, CH(C-1)).

EXAMPLE 2

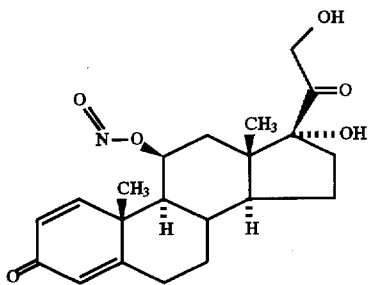

A solution of prednisolone (0.36 g; 1 mmole) in acetic acid (20 ml) was warmed up to 55° C and treated with solid sodium nitrite ester (0.28 g; 4 mmoles) for 30 seconds. The product was precipitated by addition of ice water (25 ml) and filtered. The solid was washed with water and dried over P$_2$O$_5$ in vacuo to give a white solid material. FAB-MS: (M+Li)$^+$=396.4. $^1$H-NMR (DMSO-d$_6$) d 0.51 (s, 3H, CH$_3$ (C-18)), 1.08 (s, 3H, CH$_3$ (C-19)), 4.0–4.4 (2d, 2H, CO—CH$_2$—O), 5.95 (s, 1H, CH(C-4)), 6.17 (d, 1H, CH(C-2), 6.22 (s, 1H, CH(C-11)), 6.98 (d, 1H, CH(C-1)).

EXAMPLE 3

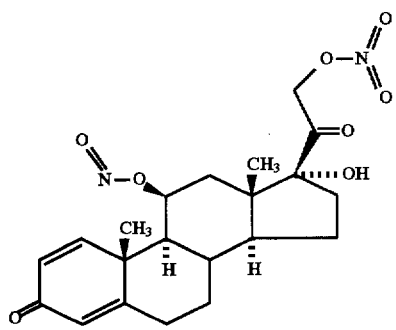

A. Preparation of prednisolone-21-nitrate ester: Fuming nitric acid (0.5 ml; d=1.49) and acetic anhydride (2 ml) were combined at −10° C. To this solution, a pre-cooled suspension of prednisolone (1 g; 2.8 mmoles) in chloroform (10 ml) was added dropwise with stirring. The progress of the reaction was monitored by TLC and HPLC. The mixture was stirred for another hour in an ice bath and poured into ice water (50 ml). The organic phase was separated and washed with water, saturated sodium bicarbonate solution and water. After drying over sodium sulfate overnight, the solid was filtered and the filtrate was taken down to dryness. The residue was purified on a Waters μBondapak column (1.9 cm×15 cm) using a linear gradient of 25–75% acetonitrile/water/trifluoroacetic acid. The desired fractions were collected and lyophilized to give 0.7 g of white material. FAB-MS: (M+Li)$^+$=412; $^1$H-NMR (DMSO-d$_6$) d 0.80 (s, 3H, CH$_3$(C-18)), 1.39 (s, 3H, CH$_3$(C-19)), 4.24 (s, 1H, CH(C-11)), 5.2–5.6(q, 2H, CO—CH$_2$—O), 5.95 (s, 1H, CH(C-4)), 6.18 (d, 1H, CH(C-2)), 7.34 (d, 1H, CH(C-1)).

B. The title compound is prepared from prednisolone-21-nitrate ester and sodium nitrite ester in acetic acid by the method of EXAMPLE 2.

EXAMPLE 4

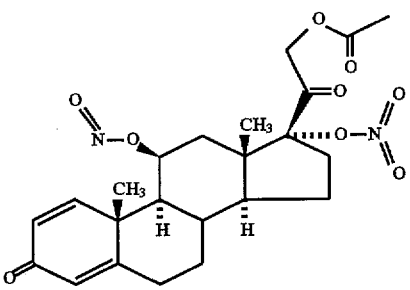

A. Preparation of prednisolone-17-nitrate ester-21-acetate: The compound is prepared from prednisolone-21-acetate (1 g; 2.5 mmoles) in the same manner as described for EXAMPLE 3 to give 0.7 g of white material. FAB-MS: (M+H)$^+$=448; $^1$H-NMR (CDCl$_3$) d1.07(s,3H, CH$_3$(C-18)), 1.45 (s,3H, CH$_3$(C-19)), 2.20 (s, 3H, CH$_3$—CO), 4.50–4.55 (m, 1H, CH (C-11)), 6.05 (s, 1H, CH, (C-4)), 6.25 (d, 1H, CH(C-2), 7.25 (d, 1H, CH (C-1)).

B. Prednisolone-17-nitrate ester-21-acetate is treated with sodium nitrite ester in acetic acid by the method of EXAMPLE 2 to produce the title compound.

EXAMPLE 5

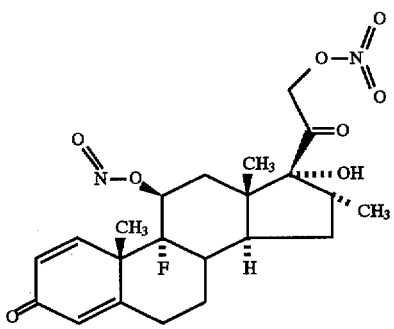

A. Preparation of 9a-fluoro-16a-methylprednisolone-21-nitrate ester: The compound is prepared from 9a-fluoro-16a-methylprednisolone (1 g; 2.5 mmoles) in the same manner as described for EXAMPLE 3 to give 0.75 g of white material. FAB-MS: (M+Li)$^+$=444; $^1$H-NMR (CDCl$_3$) d 0.91 (d, 3H, CH—CH$_3$), 1.05 (s, 3H, CH$_3$(C-18)), 1.55 (s, 3H, CH$_3$(C-19)), 4.38 (d, 1H, CH(C-11)), 5.2(q, 2H, CO—CH$_2$—O), 6.07 (s, 1H, CH(C-4)), 6.38 (d, 1H, CH(C-2)), 7.21 (d, 1H, CH(C-1)).

B. A solution of 9a-fluoro-16a-methylprednisolone-21-nitrate ester is treated with sodium nitrite ester in acetic acid by the method of EXAMPLE 2 to produce the title compound.

EXAMPLE 6

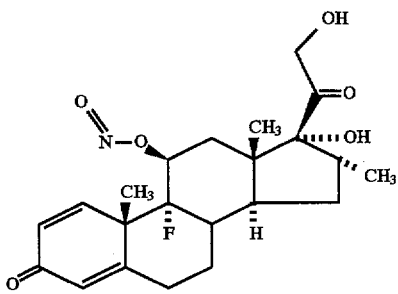

A solution of 9a-fluoro-16a-methylprednisolone is treated with sodium nitrite ester in acetic acid by the method of EXAMPLE 2 to produce the title product.

EXAMPLE 7

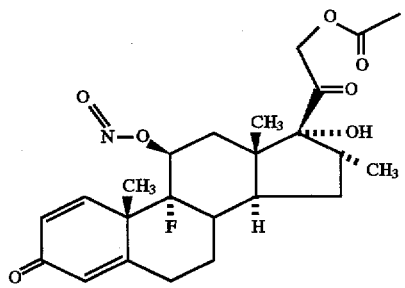

A. A solution of 9a-fluoro-16a-methylprednisolone-11-nitrite ester (0.23 g; 0.5 mmoles) in chloroform/pyridine (10 ml; 1:1) is treated with acetic anhydride (5 ml) with stirring at room temperature. The reaction is monitored by HPLC and carried out until completion. The crude product is purified by reversed-phase HPLC to generate the title compound.

B. Alternatively, The title compound is prepared from 9a-fluoro-16a-methylprednisolone-21-acetate by the method of EXAMPLE 2.

EXAMPLE 8

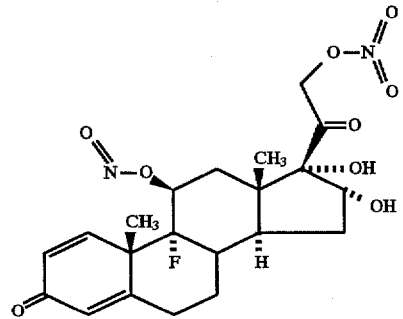

A. Preparation of 9a-fluoro-16a-hydroxyprednisolone-21-nitrate ester: The compound was prepared from 9a-fluoro-16a-hydroxyprednisolone (1 g; 2.5 mmoles) in the same manner as described for EXAMPLE 3. FAB-MS: $(M+H)^+=440$; $^1$H-NMR (DMSO-$d_6$) d 0.82 (s, 3H, CH$_3$(C-18)), 1.29 (s, 3H, CH$_3$(C-19)), 5.61 (d, 1H, CH(C-11)), 5.5–5.8(q, 2H, CO—CH$_2$—O), 5.98 (s, 1H, CH(C-4)), 6.18 (d, 1H, CH(C-2)), 7.03 (d, 1H, CH(C-1)).

B. The title compound is prepared from 9a-fluoro-16a-hydroxyprednisolone-21-nitrate ester and sodium nitrite ester in acetic acid by the method of EXAMPLE 2.

EXAMPLE 9

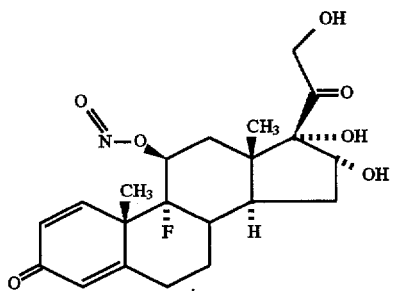

9a-fluoro-16a-hydroxy-prednisolone is treated with sodium nitrite ester in acetic acid by the method of EXAMPLE 2 to produce the title compound.

EXAMPLE 10

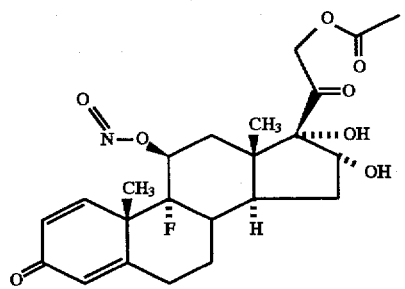

The product of EXAMPLE 9 is treated with acetic anhydride in pyridine/chloroform by the method of EXAMPLE 3 to give the title product.

EXAMPLE 11

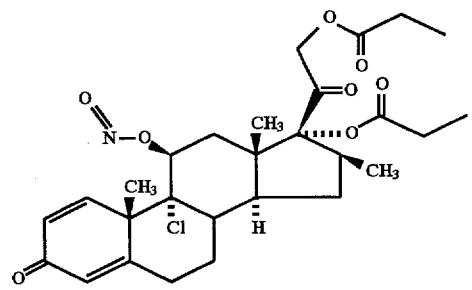

A solution of beclomethasone-17,21-dipropionate (0.01 g; 0.019 mmoles) in acetic acid (1 ml) was warmed up to 55° C and treated with solid sodium nitrite ester (0.007 g; 0.1 mmole) for 30 seconds. The product was precipitated by addition of ice water (5 ml) and filtered. The solid was washed with water and dried over $P_2O_5$ in vacuo to give a white solid material. FAB-MS: $(M+Li)^+=556.4$.

Biological Data

The subject compounds of the formula (1) have been found to be nitric oxide donors while maintaining their steroid activities and possess useful pharmacological properties as demonstrated in one or more of the following tests:

Selected compounds were tested in three in vitro and two in vivo assays. The in vitro assays consisted of the following: measuring the effect of the compounds to inhibit the increase of prostaglandins following treatment of human fetal fibroblasts cells with interleukin-1 followed by arachidonic acid, measuring the effect of the compounds on cyclic GMP in the human fetal fibroblasts, and measuring the smooth muscle relaxant activity in rat aortic rings. The in vivo assay consists of measuring the antiinflammatory properties of the compounds in the carageenan treated rat air pouch model and the relaxant activity on acetylcholine-induced bronchoconstriction in guinea-pigs.

A. In vitro inhibiton of prostaglandin $E_2$ ($PGE_2$) synthesis assay: Human fetal fibroblasts cells were treated with IL-1 for 16 hours and then with 10 mM arachidonic acid (AA). The prostaglandin $E_2$ levels were measured by an ELISA. Compounds were given at the time of addition of IL-1. This assay provides an in vitro assessment of the compound to block the induction of the proinflammatory agent prostaglandin $E_2$ ($PGE_2$):

| Treatment | $PGE_2$ (ng) |
| --- | --- |
| Basal | 3.5 |
| IL-1, AA | 40.0 |
| IL-1, AA and prednisolone (10 uM) | 9.9 |
| IL-1, AA and EXAMPLE 1 (10 uM) | 9.2 |

These data indicate that the steroids with the modifications for the generation of nitric oxide are effective at inhibiting the increase in $PGE_2$ and maintain the glucocorticoid action in the prevention of prostaglandin formation.

B. In vitro stimulation of cGMP production assay: Human fetal fibroblasts in the presence of isobutylmethylxanthine, an inhibitor of phosphodiesterase, were treated with compounds for 120 min and the intra-cellular cyclic GMP levels are measured by a radioimmunoassay. The cell line is utilized as a reporter cell assay to monitor the production of NO.

| Treatment | cyclic GMP(fm)/cell well |
| --- | --- |
| Basal | 1.8 |
| Prednisolone | 1.6 |
| EXAMPLE 1 | 4.8 |

These data show that the compounds possess the ability to increase cyclic GMP levels in the nitric oxide reporter cell assay, indicating that the compound releases nitric oxide during the treatment of the cells.

C. In vitro smooth relaxant activity assay: Selected compounds were examined for the ability to relax smooth muscle. The rat aortic ring assay was utilized as a bioassay to measure the relaxant activity. The rings were precontracted with phenylephrine (0.3 µM) and subsequently compounds were added to the tissue bath in the presence of cysteine (Cys) and $N^G$-L-nitro-arginine methyl ester (L-NAME):

In vitro smooth relaxant activity assay in the presence of Cys and L-NAME:

| Compound | Relaxation, $EC_{50}$ [µM] |
| --- | --- |
| beclomethasone dipropionate | >100 |
| beclomethasone dipropionate-11-nitrate ester | 2.0 |
| prednisolone | >100 |
| prednisolone-11-nitrate ester-21-acetate | 25.0 |
| Example 1 | 0.02 |
| Example 2 | 0.03 |
| Example 11 | 0.04 |

These data indicate that these compounds have smooth muscle relaxant activity, while the control compounds prednisolone and beclomethasone dipropionate did not show any effect as is shown in FIGS. 1 and 2.

D. In vivo anti inflammatory assay: EXAMPLE 1 was tested for antiinflammatory activity in vivo in the rat carageenan air pouch assay. Rats are injected subcutaneously with a volume of air over several days to form a pouch. Inflammation is subsequently induced in the pouch by the addition of the proinflammatory agent carageenan. The inflammation is measured by assaying the pouch fluid for prostaglandin $E_2$ by ELISA. Examples 1 at 3 mg/kg dose blocked the increase in prostaglandin $E_2$ by 60%. These data indicate that the compound possess the ability to reduce inflammation in vivo.

E. Relaxant activity on acetylcholine-induced bronchoconstriction in guinea-pigs in vivo: Effect of EXAMPLE 1 on acetylcholine-induced increase in airway resistance (RL) was studied in guinea-pigs in vivo. Animals were divided into three experimental groups. In group one (naive group), animals (n=5) were treated with aerosol acetylcholine (0.3M) at zero time and at 50 min. In group two (vehicle group), animal (n=1) was given aerosol acetylcholine at zero time, aerosol vehicle (10% ethanol/PBS) given at 70% of increased RL induced by the first acetylcholine challenge, and aerosol acetylcholine (0.3M) at 50 minutes. In group three, animals (n=3) were given aerosol acetylcholine at zero time, aerosol EXAMPLE 1 (0.2 mM) in 10% ethanol/PBS given at 70% of increased RL induced by the first acetylcholine challenge, and aerosol acetylcholine (0.3M) at 50 min. Data shown below are percentage increase in RL above the baseline. s.e mean were shown in verticle bars.

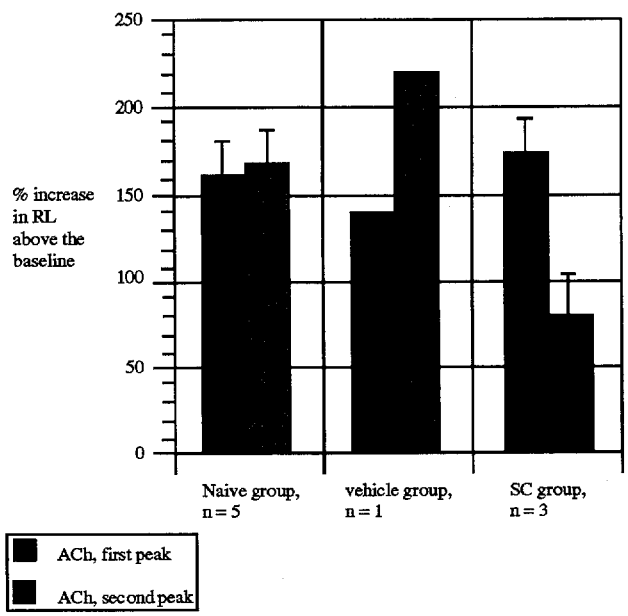
In a separate experiment, the animals were given varying concentration of EXAMPLE 1 (0.03 mM, 0.1 mM and 0.3 mM) and the results are presented below.
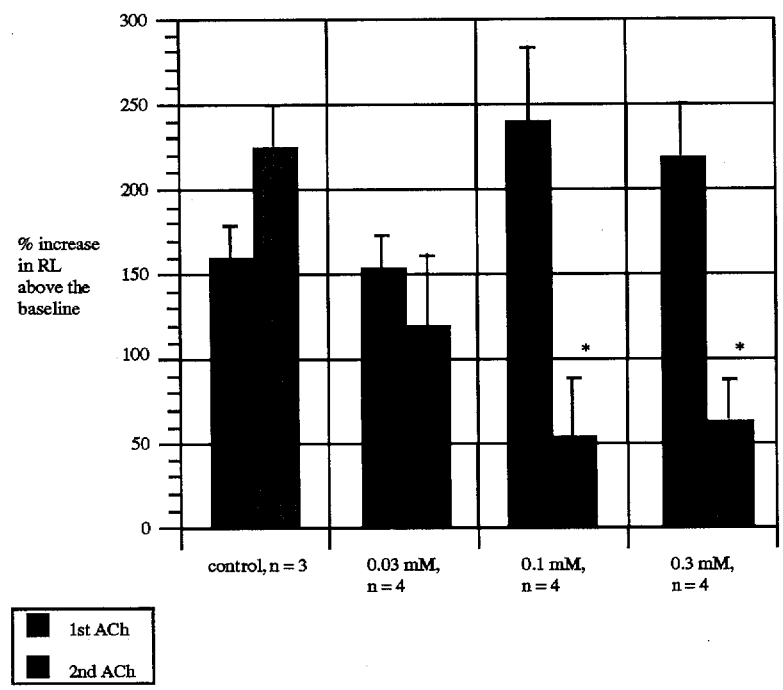
These data indicate that the glucocorticoid containing nitric oxide donating group is effective in inhibiting acetylcholine-induced increase in airway resistance (RL) in guinea-pigs in vivo in a dose-dependent manner.

What is claimed is:

1. A compound having the formula:

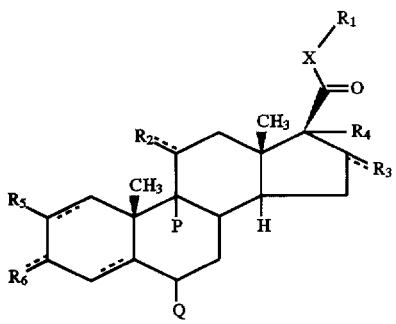

or a pharmaceutically acceptable ester or prodrugs thereof, wherein the dotted lines indicate a single or a double bond;

$R_1$ is selected from the group consisting of hydrogen, hydroxy, nitrite ester (ONO), nitrate ester (ONO$_2$), halogen, haloalkyl, nitroxyalkanoyl, sulfhydryl, lower thioalkyl, heterocyclic, lower alkoxy, alkylsilyloxy, lower alkyl, lower alkenyl and lower alkynyl wherein said group may optionally be substituted with hydroxy, halogen, lower alkyl, lower alkenyl, lower alkynyl, lower alkoxy, amino, nitro, nitril, carboxyl and haloalkyl radicals; or, $R_1$ is OCO—$R_7$ wherein $R_7$ is alkanoic acid, lower alkyl, lower alkenyl, lower alkynyl, or lower alkoxy;

$R_2$ is selected from the group consisting of hydrogen, hydroxy, oxygen, nitrite ester (ONO), nitrate ester (ONO$_2$), nitroxyalkanoyl, lower alkoxy, alkylsilyloxy, and lower alkyl wherein said group may optionally be substituted with hydroxy, lower alkyl, lower alkenyl, lower alkynyl, lower alkoxy, amino, nitro, nitril, carboxyl haloalkyl radicals or $R_2$ is OCO—$R_8$ wherein $R_8$ is alkanoic acid, lower alkyl, lower alkenyl, lower alkynyl or lower alkoxy group;

$R_3$ and $R_4$ are independently selected from the group consisting of hydrogen, hydroxy, nitrite ester (ONO), nitrate ester (ONO$_2$), nitroxyalkanoyl, lower alkyl, lower alkenyl, lower alkynyl, and lower alkoxy, wherein said group may optionally be substituted with hydroxy, lower alkyl, lower alkenyl, lower alkynyl, lower alkoxy, amino, nitro, nitril, carboxyl and haloalkyl radicals, and OCO—$R_9$ wherein $R_9$ is 2-furanyl, lower alkyl or lower alkoxy group;

$R_5$ is hydrogen or halogen;

$R_6$ is hydrogen, hydroxy, or oxygen;

P and Q are independently selected from the group consisting of hydrogen, halogen and lower alkyl;

X is lower alkyl group, or sulfur if $R_1$ is a haloalkyl; and with the proviso that at least one of the following $R_1$, $R_2$, $R_3$ or $R_4$ is a nitrite ester (ONO) and that at least one of the following $R_1$, $R_2$, $R_3$ or $R_4$ is a nitrate ester (ONO2).

2. A compound having the formula:

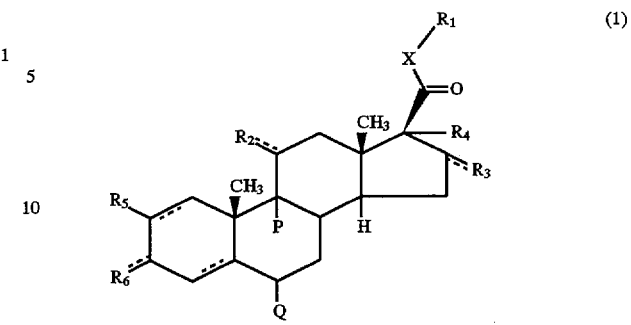

(1)

wherein the dotted lines indicates a single or a double bond;

$R_1$ is selected from the group consisting of hydrogen, hydroxy, nitrite ester (ONO), nitrate ester (ONO$_2$), halogen, haloalkyl, heterocyclic group of 2 to 5 carbon atoms and 1 to 2 hetero atoms, nitroxyalkanoyl group of 2 to 6 carbon atoms, sulfhydryl, lower thioalkyl group of 1 to 6 carbon atoms, lower alkoxy group of 1 to 6 carbon atoms, alkylsilyloxy group of 3 to 8 carbon atoms, lower alkyl group of 1 to 6 carbon atoms, wherein said group may optionally be substituted with hydroxy, halogen, lower alkyl, lower alkenyl, lower alkynyl, lower alkoxy, amino, nitro, nitril, carboxyl and haloalkyl radicals, or $R_1$ is OCO—$R_7$ wherein $R_7$ is alkanoic acid group of 2 to 6 carbon atoms, lower alkyl group of 1 to 6 carbon atoms, lower alkenyl group of 2 to 6 carbon atoms, lower alkynyl group of 2 to 6 carbon atoms, or lower alkoxy group of 1 to 6 carbon atoms group;

$R_2$ is selected from the group consisting of hydrogen, hydroxy, oxygen, nitrite ester (ONO), nitrate ester (ONO$_2$), nitroxyalkanoyl group of 2 to 6 carbon atoms, lower alkoxy group of 1 to 6 carbon atoms, alkylsilyloxy group of 3 to 8 carbon atoms, and lower alkyl group of 1 to 6 carbon atoms, wherein said group may optionally be substituted with hydroxy, lower alkyl, lower alkenyl, lower alkynyl, lower alkoxy, amino, nitro, nitril, carboxyl and haloalkyl radicals, or $R_2$ is OCO—$R_8$ wherein $R_8$ is alkanoic acid group of 2 to 6 carbon atoms, lower alkyl group of 1 to 6 carbon atoms, lower alkenyl group of 2 to 6 carbon atoms, lower alkynyl group of 2 to 6 carbon atoms or lower alkoxy group of 1 to 6 carbon atoms group;

$R_3$ and $R_4$ are independently selected from the group consisting of hydrogen, hydroxy, nitrite ester (ONO), nitrate ester (ONO$_2$), nitroxyalkanoyl group of 2 to 6 carbon atoms, lower alkyl group of 1 to 6 carbon atoms, lower alkenyl group of 2 to 6 carbon atoms, lower alkynyl group of 2 to 6 carbon atoms, and lower alkoxy group of 1 to 6 carbon atoms, wherein said group may optionally be substituted with hydroxy, lower alkyl, lower alkenyl, lower alkynyl, lower alkoxy, amino, nitro, nitril, carboxyl and haloalkyl radicals; and a group of formula OCO—$R_9$ wherein $R_9$ is 2-furanyl, lower alkyl group of 1 to 6 carbon atoms or lower alkoxy group of 1 to 6 carbon atoms;

$R_5$ is hydrogen, or halogen;

$R_6$ is hydrogen, hydroxy, or oxygen;

P and Q are independently selected from a group consisting of hydrogen, chloro, fluoro and alkyl group of 1 to 6 carbon atoms;

X is lower alkyl group, or sulfur if $R_1$ is a haloalkyl; and with the proviso that at least one of the following $R_1$, $R_2$, $R_3$ or $R_4$ is a nitrite ester (ONO) and that at least one of the following $R_1$, $R_2$, $R_3$ or $R_4$ is nitrate ester (ONO$_2$).

3. The compound as recited in claim 2 wherein; the dotted lines indicate a single or a double bond;

$R_1$ is selected from the group consisting of hydrogen, hydroxy, nitrite ester (ONO), nitrate ester ($ONO_2$), halogen, haloalkyl, sulfhydryl, heterocyclic group of 3 to 4 carbon atoms and 1 to 2 hetero atoms, nitroxyalkanoyl group of 2 to 4 carbon atoms, lower alkoxy group of 1 to 4 carbon atoms, alkylsilyloxy group of 3 to 6 carbon atoms, and lower alkyl group of 1 to 4 carbon atoms, wherein said group may optionally be substituted with hydroxy, chloro, fluoro, lower alkyl, lower alkenyl, lower alkynyl, lower alkoxy, amino, nitro, nitril, carboxyl, haloalkyl radicals, or $R_1$ is OCO—$R_7$ wherein $R_7$ is alkanoic acid group of 2 to 4 carbon atoms, lower alkyl group of 1 to 4 carbon atoms, lower alkenyl group of 2 to 4 carbon atoms, lower alkynyl group of 2 to 4 carbon atoms, or lower alkoxy group of 1 to 4 carbon atoms group;

$R_2$ is selected from the group consisting of hydrogen, hydroxy, oxygen (ketone), nitrite ester (ONO), nitrate ester ($ONO_2$), nitroxyalkanoyl group of 2 to 4 carbon atoms, lower alkoxy group of 1 to 4 carbon atoms, and lower alkyl group of 1 to 4 carbon atoms, wherein said group may optionally be substituted with hydroxy, lower alkyl, lower alkenyl, lower alkynyl, lower alkoxy, amino, nitro, nitril, carboxyl, haloalkyl radicals; or $R_2$ is OCO—$R_8$ wherein $R_8$ is alkanoic acid group of 2 to 4 carbon atoms, lower alkyl group of 1 to 4 carbon atoms, lower alkenyl group of 2 to 4 carbon atoms, lower alkynyl group of 2 to 4 carbon atoms or lower alkoxy group of 1 to 4 carbon atoms;

$R_3$ and $R_4$ are independently selected from the group consisting of hydrogen, hydroxy, nitrite ester (ONO), nitrate ester ($ONO_2$), nitroxyalkanoyl group of 1 to 4 carbon atoms, lower alkyl group of 1 to 4 carbon atoms, lower alkenyl group of 2 to 4 carbon atoms, lower alkynyl group of 2 to 4 carbon atoms, and lower alkoxy group of 1 to 4 carbon atoms, wherein said group may optionally be substituted with hydroxy, lower alkyl, lower alkenyl, lower alkynyl, lower alkoxy, amino, nitro, haloalkyl radicals and OCO—$R_9$ wherein $R_9$ is 2-furanyl, lower alkyl group of 1 to 4 carbon atoms or lower alkoxy group of 1 to 4 carbon atoms;

$R_5$ is hydrogen or halogen;

$R_6$ is hydrogen, hydroxy, or oxygen;

P and Q are independently selected from a group consisting of hydrogen, chloro, fluoro or alkyl group of 1 to 4 carbon atoms;

X is a methylene group or sulfur if $R_1$ is a fluoromethyl group; and with the proviso that at least one of the following $R_1$, $R_2$, $R_3$ or $R_4$ is a nitrite ester (ONO) and that at least one of the following $R_1$, $R_2$, $R_3$ or $R_4$ is nitrate ester (ONO2).

4. The compound as recited in claim 3 wherein;
the dotted lines indicate a single or a double bond;

$R_1$ is selected from the group consisting of hydrogen, hydroxy, nitrite ester (ONO), nitrate ester ($ONO_2$), chloro, sulfhydryl, N-methylpiperazin-1-yl, trimethylsilylmethyloxy, t-butyldimethylsilyloxy, lower alkyl group of 1 to 4 carbon atoms, or $R_1$ is OCO—$R_7$ wherein $R_7$ is propanoic acid, methyl or ethyl group;

$R_2$ is selected from the group consisting of hydroxy, oxygen, nitrite ester (ONO), and nitrate ester ($ONO_2$);

$R_3$ and $R_4$ are independently selected from the group consisting of hydrogen, hydroxy, nitrite ester (ONO), nitrate ester ($ONO_2$), methyl, and OCO—$R_9$ wherein $R_9$ is ethoxy, methyl, or ethyl;

$R_5$ is hydrogen;

$R_6$ is hydroxy or oxygen;

P and Q are independently selected from a group consisting of hydrogen, chloro, fluoro and methyl group;

X is methylene; and with the proviso that at least one of the following $R_1$, $R_2$, $R_3$ or $R_4$ is a nitrite ester (ONO) and that at least one of the following $R_1$, $R_2$, $R_3$ or $R_4$ is nitrate ester (ONO2).

5. The compound as recited in claim 1 wherein the compound is selected from the group consisting of:

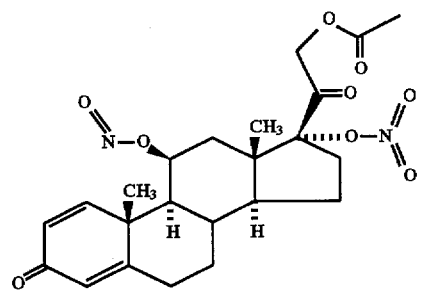

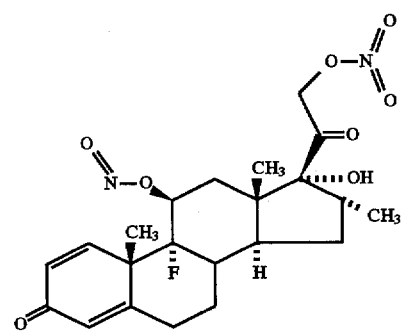

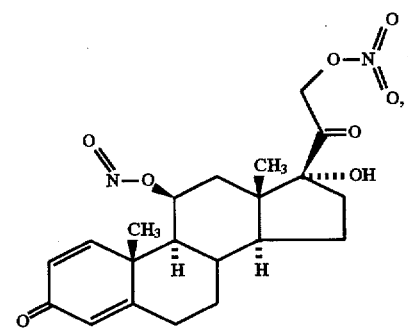

and

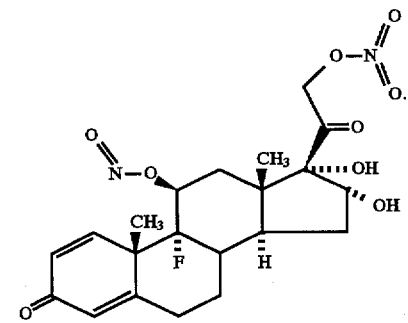

6. A method of treating a patient with inflammation by administering a therapeutically effective amount of the compound as recited in claims 1, 2, 3, 4 or 5.

7. The method of claim 6 wherein said patient also has undesired smooth muscle contractions.

8. A pharmaceutical composition comprising a compound of claim 1 together with a pharmaceutically acceptable carrier.

9. A pharmaceutical composition comprising a compound of claim 2 together with a pharmaceutically acceptable carrier.

10. A pharmaceutical composition comprising a compound of claim 3 together with a pharmaceutically acceptable carrier.

11. A pharmaceutical composition comprising a compound of claim 4 together with a pharmaceutically acceptable carrier.

12. A pharmaceutical composition comprising a compound of claim 5 together with a pharmaceutically acceptable carrier.

* * * * *